United States Patent [19]

Navia et al.

[11] Patent Number: 5,156,621
[45] Date of Patent: Oct. 20, 1992

[54] STENTLESS BIOPROSTHETIC CARDIAC VALVE

[76] Inventors: Jose A. Navia; Domingo S. Liotta; Felix O. Caivano, all of Suipacha 1308, Buenos Aires, Argentina

[21] Appl. No.: 670,479

[22] Filed: Mar. 15, 1991

Related U.S. Application Data

[63] Continuation of Ser. No. 279,058, Dec. 1, 1988, abandoned.

[30] Foreign Application Priority Data

Mar. 22, 1988 [AR] Argentina .............................. 310368

[51] Int. Cl.⁵ .............................................. A61F 2/24
[52] U.S. Cl. ...................................................... 623/2
[58] Field of Search ........................................... 623/2

[56] References Cited

U.S. PATENT DOCUMENTS

| | | | |
|---|---|---|---|
| 3,548,418 | 12/1970 | Angell et al. | 623/2 |
| 4,084,268 | 4/1978 | Ionescu et al. | 623/2 |
| 4,790,844 | 12/1988 | Ovil | 623/2 |

FOREIGN PATENT DOCUMENTS 2355492  1/1978  France .................................... 623/2

OTHER PUBLICATIONS

Navia, J. A. et al., "Low profile bioprosthesis for cardiac valve replacement: hydraulic and hemodynamic studies", Medical Instrumentation, vol. 16, No. 1, 1982.

Yacoub, M. H. et al., "A new technique for replacement of the mitral valve by a semilunar valve homograft," J. of Thoracic and Cardiovasc. Surgery, vol. 58, No. 6, pp. 859-869, Dec. 1969.

Athanasuleas, C. L. et al., "The autologous rectus sheath cardiac valve," J. of Thoracic and Cardiovasc. Surgery, vol. 65, No. 1, pp. 118-123, Jan. 1973.

O'Brien, M. F. et al., "Heterograft aortic valves for human use," J. of Thoracic and Cardiovasc. Surgery, vol. 53, No. 3, pp. 392-397, Mar., 1967.

Primary Examiner—David Isabella
Attorney, Agent, or Firm—Collard & Roe

[57] ABSTRACT

A self-supporting cardiac valve bioprosthesis of the type fixable to the patient's aortic ring for replacing an explanted valve. The bioprosthesis consists of a tubular body having a flow passageway therethrough and having a proximal and a distal end. A multi-valve obturator is located adjacent the proximal end of the tubular body for closing the flow passageway. Each valve of the multi-valve obturator is capable of rotating about a fulcrum adjacent an outer circumference of the flow passageway. A suture ring is provided having a continuous annular cord forming the fulcrum of each valve of the multi-valve obturator which cord is directly fixable to a patient's aortic ring. A textile coating compatible with the human body coats the outer surface of the tubular body and the continuous annular cord.

7 Claims, 2 Drawing Sheets

STENTLESS BIOPROSTHETIC CARDIAC VALVE

This is a continuation of copending application Ser. No. 07/279,058 filed on Dec. 1, 1988 now abandoned.

BACKGROUND OF THE INVENTION

1. Field of the Invention

The instant invention relates to a bioprosthetic cardiac valve for acting in the human blood system. More particularly, the invention relates to a self-supporting cardiac valve prosthesis, the design and structure of which make it perfectly suitable for replacing an explanted natural valve.

2. Description of Prior Art

In early studies, approximately until 1960, the normal cardiac valves were described as membranes carrying out a fully passive function depending on pressure and flow variations. Later, several works disclosed the outstanding active features of valve function. In these studies, the aortic cusps (or aortic valve per se) and the aortic root constituted a functional unit.

These papers described the aortic root from a geometrical viewpoint as a truncated cone, the side walls of which are comprised by the Valsalva sinuses; the upper limit is a circumferential line adjacent to the aortic cusps commissures, called the "sinus ridge" or "aortic ridge". The lower limit is comprised by another circumference, a virtual line, adjacent to the nadirs of the aortic valve cusps (leaflets). The prior art also discloses changes existing in the sinus ridge and in the dimensions of the aortic valve nadires during the cardiac cycle, as well as the stress to which the aortic valve cusps are subjected to during such a cycle. Furthermore, experimental work carried out on animals, including hemodynamic angiographic studies have shown that, in general, at a half of the ventricular systole, the diameter of the basal portion of the aortic valve decreases, while the diameter of the aortic ridge (aortic valve commissural plane) increases.

In humans, the behavior of aortic valves has been studied from two radiological positions through cineangiography (30 degrees right anterior oblique position and 60 degrees left anterior oblique position). These studies have demonstrated that the aortic root movements are changing from diastole to systole, frontal-caudally, dorsum-ventrally and from left to right. Frontal-caudal movement is angiographically expressed by a lowering displacement, and dorsal-ventral movement by a forward displacement. The basal portion of the aortic root (nadir) has a gradual diameter decrease during systole, while the commissural plane increases its diameter, and its maximum value is taken at the half of systole. During diastole, these movements are reversed.

On the other hand, the height of the three Valsalva sinuses does not vary simultaneously in the same direction. The movement is reciprocating: a height increase in the right sinus is accompanied by a decrease in the left sinus and, at a given point in time, they are equal. In addition, during the systole period, the shape of the radiological images of the Valsalva sinuses vary; they pass from a globular shape to a straight configuration, in an alternating manner. Therefore, the general configuration of the aortic root at the end of a diastole adopts a geometrical shape similar to a cylinder and, at the end of the systole, its shape is that of an inverted (base up) truncated cone.

During systole, the movement of the aortic valve nadires would be basically influenced by the contractility of the outlet tract of the left ventricle dependent on the cardiac dynamics. Contrary to expectations, the movement of the aortic nadires during systole would not be absolutely uniform due to anatomic relationships. The nadir of the right cusp accompanies the movements of the ventricle septum. Because both the nadirs of the left cusp, and the non-coronary cusp, are integrated to the fibrous tissue of the anterior mitral leaflet and through it to the central fibrous body of the aortoventricle membrane, little movement is provided.

During ventricular systole, the commissural plane of the aortic valve (sinus ridge) has an expansion movement opposed to that of aortic nadires, which depends on the blood volume of the left ventricle and on aortic pressure (volume-pressure dependent). During the post-extrasystole beat, the mentioned movements are stressed, with a lower diameter of the aortic ring nadires (left ventricular contractility increase) and a higher diameter of the commissural plane (related to both left ventricular stroke volume and to the arterial pressure). The outstanding physiology of both the aortic valve and the aortic root was the main objective which promoted the development of a stent-less aortic valve prosthesis. The aortic valve cusps (homologue and heterologue) are directly implanted in the aortic root of the receiving patient.

Mechanical valve prostheses employing metal or plastic components has created multiple problems such as clot formation and the need for subjecting the patient to a permanent treatment with anticoagulants. Later, stented bioprostheses were introduced, such as that disclosed in U.S. Pat. No. 4,079,468, which comprised a low profile support and a porcine aortic valve. A support frame for cardiac tissue valves is disclosed in U.S. Pat. No. 4,259,753.

Although biological valves prostheses eliminated problems due to rejection and clot formation, they nevertheless caused different problems such as reduction of the cross-section (aortic valvular area) and, consequently, a reduction in blood flow. As a consequence, an increase in pressure gradient between the left ventricle and the aorta takes place, due to the presence of the valve support. Furthermore, the flexibility of aortic commissures decrease in stented biological prostheses resulting in a higher stress than that resulting from their normal function.

SUMMARY OF THE INVENTION

It is an object of the invention to provide an extremely simple and efficient prosthesis, in the form of a biological low-profile valve prosthesis, based on anatomic studies of the aortic valve.

It is a further object to provide a valve prosthesis having no intermediate support and which is based on physiological studies of the integral function of the aortic root (it must be noted that, from the anatomic and functional point of view, the two structures—aortic root and aortic valve cusps-result normally in an inseparable unit).

Accordingly, these and other related objects are accomplished by a self-supporting (stentless) cardiac valve bioprosthesis of the type which is attachable to a patient's aortic ring and which replaces an explanted valve. The bioprosthesis comprises a tubular body defining a flow passageway therethrough which body has a proximal and a distal end.

A multi-valve obturator is positioned adjacent to the proximal end of the tubular body for opposing the flow passageway. Each valve of the multi-valve obturator is capable of rotating or pivoting about a fulcrum adjacent the outer circumference of the flow passageway. A suture ring is provided at the proximal end of the tubular body which suture ring has a continuous annular cord forming the fulcrum for each valve of the multi-valve obturator. The annular cord is capable of being directly fixed to the patient's aortic ring. The outer surface of both the tubular body and the annular cord is coated with a textile coating compatible with the human body. In addition, the tubular body has notches extending from its distal end toward the proximal end thereof, thereby defining skirts for anchoring the tubular body to the patient's aortic root.

Based on the functional anatomic features of the aortic valve, the present invention provides a bioprosthesis for aortic positioning. Some references in the prior art recite the direct implantation of an aortic valve in the aortic root (Barrat Boyes, Donald Ross, etc.). However, the prosthesis of the invention differs basically from those of the prior art in that its outer surface as well as the suture ring, are coated by a thin "Dacron" cloth this allows a progressive reliable attachment to the aortic root tissues of the patient. In addition, it allows the use of heterologue aortic valves, especially porcine aortic valves.

It is to be noted that, porcine aortic valves and valvular prosthesis are used worldwide, such use includes the fixing and preserving of the biological tissues thereof in glutaraldehyde solutions employing techniques originally developed by Carpentier et al. The self-supporting valve bioprosthesis (stent-less) of the invention is of the type which, once sutured to the patient's aortic ring for replacing an explanted valve, comprises the annular fulcrum of a valve obturator.

These and other objects and features of the present invention will become apparent from the following detailed description considered in connection with the accompanying drawings, which disclose one embodiment of the invention. It is to be understood that the drawings are to be used for the purpose of illustration only, and not as a definition of the limits of the invention.

BRIEF DESCRIPTION OF THE DRAWINGS

In the drawing, wherein similar reference characters denote similar elements throughout the several views.

DESCRIPTION OF THE PREFERRED EMBODIMENT

Figure 1:
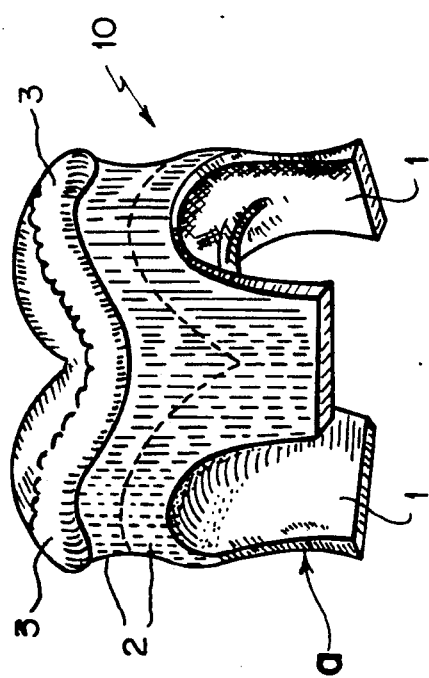
FIG. 1 is a partial perspective elevation view of the bioprosthesis of the invention, in which the general configuration and arrangement of the different elements are shown.
Figure 3:
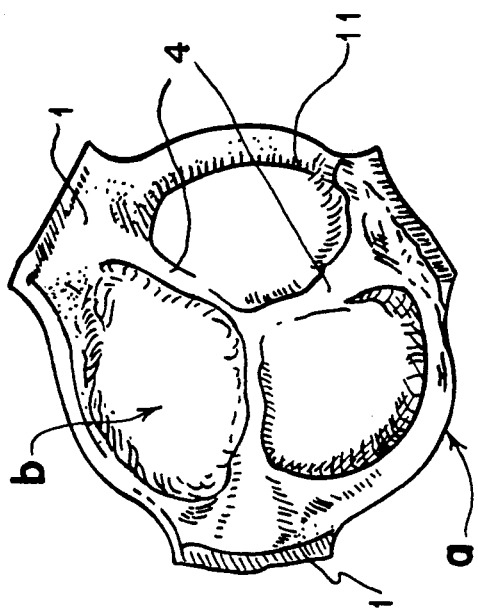
FIG. 3 is a bottom view of the bioprosthesis.
Figure 2:
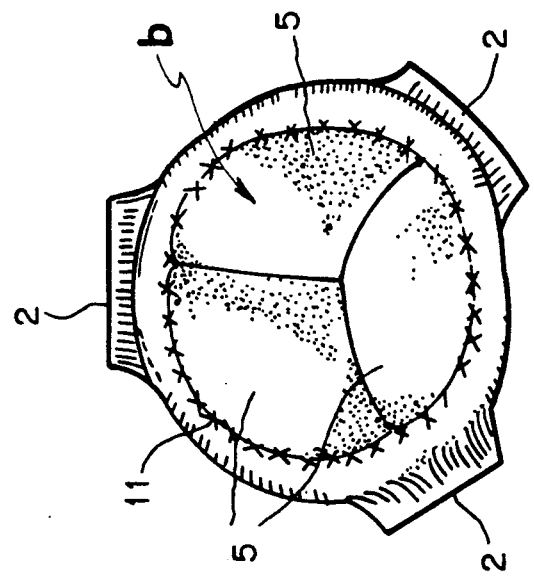
FIG. 2 is a plan view of the bioprosthesis of the invention showing the valve obturator corresponding to an aortic valve.
Figure 4:
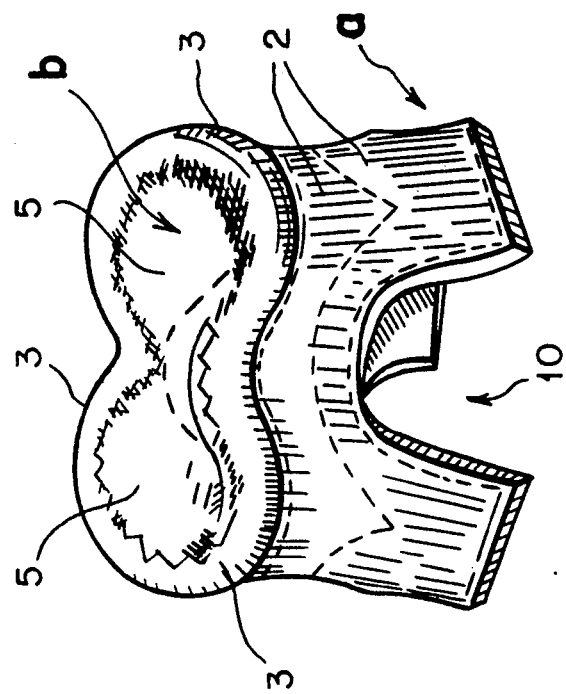
FIG. 4 is a partial perspective view of the bioprosthesis of the invention, seen from its bottom portion, clearly showing the notches forming the anchoring skirts.
Figure 5:
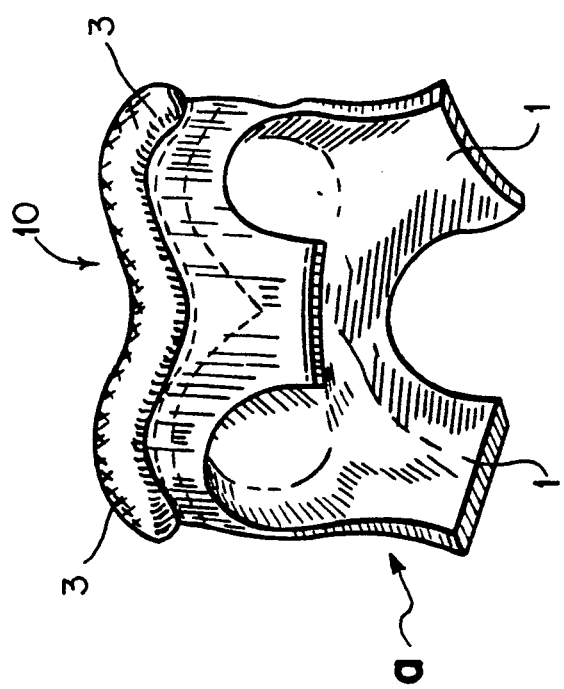
FIG. 5 is a front and upper perspective view of the bioprosthesis of the invention showing the annular continuous cord configuration acting as suture ring, and the textile layer coating the whole outer surface of the tubular body, with the coating reaching the cord.

Referring to FIGS. 1-5, there is shown the bioprosthesis of the invention generally denoted as 10, which comprises a heterologous valve assembly, of animal origin, such as a porcine aortic valve which may be pre-treated with glutaraldehyde solution.

Such bioprosthesis 10 comprises a tubular body "a" and a valve obturator "b". It is characterized in that the annular fulcrum of the valve obturator "b" of valve assembly 12 is fixed to the receptor aortic ring via a suture ring 3 adjacent the proximal edges of body "a", and is attached to a tubular body "a" of valve 12 which body "a" is of animal origin. The proximal edges of body "a" are adjacent valve suture ring 3 is in the form of a continuous annular cord. The cord of suture ring 3, as well as the outer faces of the tubular body "a", have a textile coating 2 which is biologically compatible with the tissues receiving the prosthesis.

Valve assembly 10 is fixable to the patient's aortic ring and aortic root to replace an explanted valve, and comprises annular fulcrum 11 of valve obturator "b" which is comprised of three valve cusps 5, the lips of which reciprocate in relation to reverse limiting stops 4 defining a perfect closure. The annular fulcrum 11 of valve obturator "b" is fixed to the aortic ring since the invention does not use any intermediate support which, among other things, avoids rigidity thereof and makes the structure flexible. The outer wall of fulcrum 11, on a proximal edge adjacent the valve obturator "b", form a continuous annular cord or fabric coated DACRON ®, which is a registered trademark for polyester synthetic fiber, suture ring 3. Suture ring 3 is a precise adaptation to the size and level of the aortic anatomic ring including providing the corresponding undulations thus allowing the unaltered physiology of the aortic ring.

Unlike conventional biological prosthesis, the prosthesis of the invention is completely flexible for mating with the aortic root physiology. Its cusps 5 and commissure are not subjected to any kind of additional stress since there is no intermediate rigid nor semi-rigid support. This support may give rise to the initiation of tissue stress, as well as to the more frequent localization of calcium nuclei and their subsequent breakage. Further, it is important to note that, since the bioprosthesis of the invention has no support, when prosthesis 10 is implanted at the patient's ring, it does not affect the anatomy of the Valsalva sinuses due to the fact that the design of the cord of suture ring 3 results in it not being in contact with the Valsalva sinuses. Rather, the cord's undulated design fits on the original ring of the explanted valve bearing a different pathology.

The outer commissural portion of the self-supporting prosthesis, i.e., the outer faces of tubular body "a" are coated with a thin DACRON ®, which is a registered trademark for polyester synthetic fiber, cloth or yarn 2, of the velour type or the like, also extending to coat or cover the cord of suture ring 3. This allows its adaptation, suture, adhesion and incorporation to the aortic wall through progressive invasion of the patient's connective tissue. It further permits the surgical trimming off of excess prosthetic tissue avoiding encroachment with the patient's coronary ostia. Tubular body "a", from the cord of suture ring 3 to the distal edge, has notches between which anchoring skirts 1 are defined. The prosthesis 10 of the invention makes it possible to use valve sizes similar to those of the explanted valve, since there is no intermediate support decreasing the useful valve area (as happens in all bioprostheses or mechancial prostheses in use at present), thus decreasing the gradient across the valve prosthesis. The use of porcine valves, previously treated with glutaraldehyde solution, is highly desirable from a practical viewpoint, since there is no limitation in the amount available nor in their diameter range, thus allowing a precise adaptation to the receptor's tissues.

The first step in the technique for mounting the bioprosthesis of the invention is making a "U"-shaped cut in the wall of the Valsalva sinuses, thoroughly controlling the height of the three commissures. Then an outer aortic wall is coated with a DACRON®, which is a registered trademark for polyester synthetic fiber, tubular mesh (cloth), matching the configuration of the wall distal edge. To this end, the cloth should be cut and folded 2 mm inwards, being supported close to the wall by means of a continuous suture made of white braided polyester 5-0. A linear suture is then made on the central segment, between the distal and proximal edges, mating the undulated configuration.

The suture ring 3 is prepared by making a continuous dotted, slightly undulated line 1 mm above the proximal edge. The suture ring 3 filler is introduced therebelow, being supported by a continuous dotted suture 1 mm from the proximal edge. The filler should be 2-3 mm in height and approximately 2 mm in thickness.

The filler material is the same material as the suture itself, namely, Dacron®.

While one embodiment and example of the present invention has been illustrated and described, it is obvious that many changes and modifications may be made thereunto, without departing from the spirit and scope of the invention.

What is claimed is:

1. A self-supporting stentless cardiac valve bioprosthesis of the type fixable to a patient's aortic ring for replacing an explanted valve comprising:
    a tubular body of animal origin defining a flow passageway therethrough having a proximal and a distal end;
    a multi-valve obturator adjacent the proximal end of the tubular body for closing the flow passageway, each valve of the multi-valve obturator capable of rotating about a fulcrum adjacent an outer circumference of the flow passageway;
    a suture ring having a continuous annular cord disposed adjacent the fulcrum of each valve of the multi-valve obturator and being directly fixable to the patient's aortic ring; and
    a textile coating compatible with the human body coating an outer surface of the tubular body and said continuous annular cord.

2. The bioprosthesis as claimed in claim 1, wherein said multi-valve obturator has three valves corresponding to a natural aortic valve.

3. The bioprosthesis as claimed in claim 1, wherein the tubular body has notches extending from its distal end toward the proximal end defining therebetween skirts for anchoring the tubular body to a patient's aortic root.

4. The bioprosthesis as claimed in claim 1, wherein the multi-valve obturator is a porcine aortic valve.

5. The bioprosthesis as claimed in claim 1, wherein the continuous annular cord forming the fulcrum of each valve of the multi-valve obturator as well as an outer surface of the tubular body are coated by a synthetic fiber.

6. The bioprosthesis as claimed in claim 5, wherein the synthetic fiber is in the form of a thin polyester synthetic fiber cloth.

7. The bioprosthesis as claimed in claim 1, wherein the continuous annular cord is undulated, having a shape and size matching those of the aortic ring into which it is fixable.

* * * * *